(12) United States Patent
Busey et al.

(10) Patent No.: US 12,106,827 B1
(45) Date of Patent: Oct. 1, 2024

(54) SYSTEMS AND METHODS FOR PREDICTING RESULTS OF A MANUFACTURING PROCESS FOR GENERATING BIOLOGICAL STRUCTURES

(71) Applicant: Form Bio Inc., Austin, TX (US)

(72) Inventors: Andrew Busey, Austin, TX (US); Alexander Joseph Titus, Manchester, NH (US); Nicholas Ketz, Madison, WI (US); Austin Lewis Day, Somerville, MA (US); Amicia Devin Elliott, Burien, WA (US)

(73) Assignee: Form Bio Inc., Austin, TX (US)

( * ) Notice: Subject to any disclaimer, the term of this patent is extended or adjusted under 35 U.S.C. 154(b) by 0 days.

(21) Appl. No.: 18/335,875

(22) Filed: Jun. 15, 2023

(51) Int. Cl.
*G01N 33/48* (2006.01)
*G16B 30/20* (2019.01)
*G16B 40/20* (2019.01)

(52) U.S. Cl.
CPC ............. *G16B 30/20* (2019.02); *G16B 40/20* (2019.02)

(58) Field of Classification Search
None
See application file for complete search history.

(56) References Cited

PUBLICATIONS

Nguyen, Tam Ngoc Thanh. Systems Engineering for Viral Vector Manufacturing. Diss. Massachusetts Institute of Technology, 2023.*
Canova, Christopher T., Pavan K. Inguva, and Richard D. Braatz. "Mechanistic modeling of viral particle production." Biotechnology and Bioengineering 120.3 (2023): 629-641.*
Screen captures from YouTube clip entitled "A friendly introduction to Recurrent Neural Networks," 4 pages, Uploaded Aug. 18, 2017 by user "Serrano. Academy," Retrieved from Internet: <https://youtu.be/UNmqTiOnRfg?si=VaKICmaW6wQGydAz>.*
Screen captures from YouTube clip entitled "Linear Regression in 2 minutes," 3 pages, Uploaded Nov. 28, 2021 by user "Visually Explained," Retrieved from Internet: <https://www.youtube.com/watch?v=CtsRRUddV2s>.*
Mowbray, Max, et al. "Machine learning for biochemical engineering: A review." Biochemical Engineering Journal 172 (2021):108054.*
Bryant, Drew H., et al. "Deep diversification of an AAV capsid protein by machine learning." Nature Biotechnology 39.6 (2021): 691-696.*

* cited by examiner

*Primary Examiner* — Anna Skibinsky
(74) *Attorney, Agent, or Firm* — Esplin & Associates, PC (57) ABSTRACT

A system and method for predicting results of a manufacturing process for generating biological structures are disclosed. Exemplary implementations may include: store one or more models configured to simulate a bioreactor device to determine predicted results of a manufacturing process to generate biological structures; obtain an input genomic construct; obtain values of operational parameters associated with the bioreactor device; provide the input genomic construct and the values of operational parameters as input to the stored model(s); obtain outputs from the model(s) including the predicted results of the manufacturing process based on a first simulation of the manufacturing process; generate recommendations based on the outputs of the model(s); provide the outputs from the model(s) and the generated recommendations; and/or other exemplary implementations.

14 Claims, 4 Drawing Sheets

SYSTEMS AND METHODS FOR PREDICTING RESULTS OF A MANUFACTURING PROCESS FOR GENERATING BIOLOGICAL STRUCTURES

FIELD OF THE DISCLOSURE

The present disclosure relates to systems and methods for predicting results of a manufacturing process for generating biological structures.

BACKGROUND

Methods for determining and analyzing genomic information are known (e.g., DNA sequencing, etc.). Genomic information may be tested using various programs and/or methods for accuracy and/or quality prior to production.

SUMMARY

Construct design and production for therapeutic remedies may pose many challenges. Challenges may include manufacturing failures, production of ineffective/defective gene therapies, low yields, and/or other types of problems. Manufacturing gene therapies may be expensive and time consuming, hence there is a need to optimize constructs used for gene therapies prior to manufacturing. Analysis on the construct design, manufacturing tools and conditions (i.e., a bioreactor), and/or other aspects of manufacturing may aid to prevent manufacturing failures and inefficiency. The analysis may determine changes to the construct design, manufacturing tools and conditions, and/or other aspects of manufacturing to enhance manufacturing outcomes while reducing the costs associated with multiple manufacturing trials. One way to achieve this enhancement is to mathematically model the manufacturing process to predict results, identify problems within the construct design, and/or provide recommendations for improvement.

One or more aspects of the present disclosure include a system for predicting results of a manufacturing process for generating biological structures. The system may include one or more hardware processors configured by machine-readable instructions, electronic storage, and/or other components. Executing the machine-readable instructions may cause the one or more hardware processors to predict results of a manufacturing process for generating biological structures. The machine-readable instructions may include one or more computer program components. The one or more computer program components may include one or more of an input component, a model component, a recommendation component, an output component, and/or other components.

The electronic storage may store one or more models configured to simulate a bioreactor device to determine predicted results of a manufacturing process to generate biological structures. The bioreactor device may house a biologically active environment that supports biochemical transformations. The manufacturing process may be performed in the biologically active environment housed within the bioreactor device. Inputs to the model(s) may include a genomic construct, values of operational parameters associated with the bioreactor device, and/or other information. Outputs of the one or more models may specify the predicted results of the manufacturing process.

The input component may obtain an input genomic construct and/or other information. The input genomic construct may include a nucleic acid sequence defined by an order of nucleotides. The nucleic acid sequence may impact the formation of biological structures generated by the manufacturing process.

The input component may obtain values of operational parameters associated with the bioreactor device and/or other information. The values of operational parameters may describe the bioreactor device, conditions of the biologically active environment house within the bioreactor device, and/or other aspects of the bioreactor device. Descriptions of the conditions of the biologically active environment may include descriptions of contents included in the biologically active environment.

The model component may provide the input genomic construct, the values of operational parameters, and/or other information as input to the stored model(s). The one or more models may be configured to simulate the manufacturing process. The simulation may be for the manufacturing process as performed in the biologically active environment housed within the bioreactor device as described by the values of operational parameters. The model(s) may simulate the manufacturing process to determine the predicted results of the manufacturing process.

The model component may obtain outputs from the one or more models. The outputs from the one or more models may include the predicted results of the manufacturing process based on a first simulation of the manufacturing process. The results may describe expected biological structures to be generated by the manufacturing process.

The recommendation component may generate recommendations based on the outputs of the one or more models and/or other information. The recommendations may specify modifications to at least one of the input genomic construct, the values of operational parameters, and/or other information provided as input to the one or more models. The recommendations may be generated to increase productivity of the manufacturing process.

The output component may be configured to provide the outputs from the one or more models, the generated recommendations, and/or other information.

As used herein, any association (or relation, or reflection, or indication, or correspondency) involving servers, processors, client computing platforms, and/or another entity or object that interacts with any part of the system and/or plays a part in the operation of the system, may be a one-to-one association, a one-to-many association, a many-to-one association, and/or a many-to-many association or N-to-M association (note that N and M may be different numbers greater than 1).

These and other features, and characteristics of the present technology, as well as the methods of operation and functions of the related elements of structure and the combination of parts will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a,' 'an,' and 'the' include plural referents unless the context clearly dictates otherwise.

DETAILED DESCRIPTION

Figure 1:
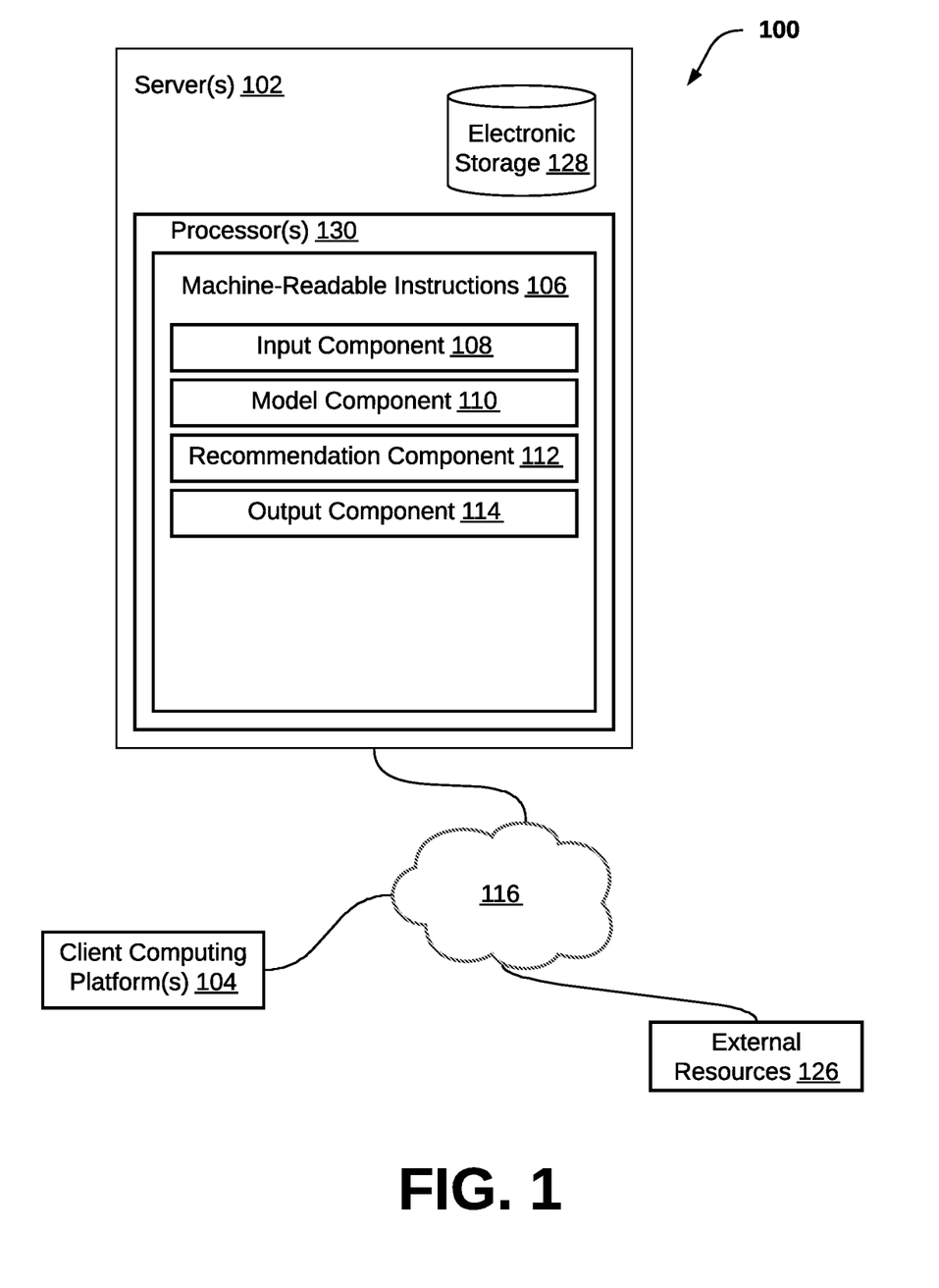
FIG. 1 illustrates a system for predicting results of a manufacturing process for generating biological structures, in accordance with one or more implementations.

FIG. 1 illustrates a system 100 configured to predict results of a manufacturing process for generating biological structures, in accordance with one or more implementations. In some implementations, system 100 may include one or more servers 102. Server(s) 102 may include electronic storage 128, one or more processors 130, and/or other components. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Server(s) 102 may be configured by machine-readable instructions 106. Machine-readable instructions 106 may include one or more instruction components. The instruction components may include computer program components. The instruction components may include one or more of input component 108, model component 110, recommendation component 112, output component 114, and/or other instruction components.

Electronic storage 128 may store one or more models configured to simulate a bioreactor device to determine predicted results of a manufacturing process that generates biological structures. Inputs to the model(s) may include a genomic construct, values of operational parameters associated with the bioreactor device, and/or other information. Outputs of the model(s) may specify the predicted results of the manufacturing process. The manufacturing process may include synthesizing, producing, and/or otherwise assembling biomaterials, biomolecules, and/or other biological structures. The biological structures generated by the manufacturing process may be used for therapeutic purposes (e.g., pharmaceuticals, gene therapies, etc.), consumption (e.g., food and beverage processing), industrial applications, and/or other uses. In some implementations, the manufacturing process may generate the biological structures using organic materials, chemical substances, and/or other components. The organic materials, chemical substances, and/or other components may be added to the bioreactor device for incorporation and/or transformation into biological structures. The bioreactor device may house a biologically active environment that supports biochemical transformations and/or other types of transformations included in the manufacturing process. The manufacturing process may be performed in the biologically active environment housed within the bioreactor device.

The stored model(s) may be configured to simulate the bioreactor device by mathematical modeling the manufacturing process performed in the bioreactor. The model(s) may be configured to assign mathematical values to individual aspects of the manufacturing process and/or aspects of the bioreactor device. Subsequently, the model(s) may be configured to calculate, analyze, and/or otherwise evaluate the interactions between the assigned mathematical values to generate predictions regarding the products of the manufacturing process. In some implementations, the predictions may be based on empirical information detailing observed performances of manufacturing processes in bioreactor devices. The empirical information may describe the observed results of manufacturing processes, genomic constructs used in the manufacturing processes, settings pertaining the to the bioreactor device, contents added to the bioreactor device, and/or other information. The use of the term "observed" may indicate the actual performance of a manufacturing process using a bioreactor device rather than a simulated and/or modeled performance of a manufacturing process. By way of non-limiting illustration, the actual performance of a manufacturing process may include bench-scale testing, industrial-scale production, an/or other methods of producing biological structures.

In some implementations, individual models may be associated with and/or provide outputs describing individual aspects of the predicted results of the manufacturing process. By way of non-limiting illustration, a first model may provide outputs describing a predicted ratio between full capsids and empty capsids generated by the manufacturing process. A second model may provide outputs describing a predicted quantity of truncated genomes included in capsids generated by the manufacturing process. The quantity of truncated genomes included in capsids may be a percentage of capsids having truncated genomes. A third model may provide outputs describing predicted mRNA and/or end protein expression. A fourth model may describe chimeric DNA included in capsids generated by the manufacturing. A fifth model may describe a predicted immunotoxicity response for utilization of biological structures (e.g., immune response to gene therapies) generated by the manufacturing process. It is to be expressly understood, however, that the specified models are for the purpose of illustration and description only and are not intended as a definition of the limits of the invention.

In some implementations, the stored model(s) may include one or more trained machine learning model(s). An individual trained machine learning model may be configured to generate outputs including results of simulated manufacturing processes based on inputted genomic constructs and values of operational parameters. The trained machine learning model may be trained using training information. Training information may include the empirical information detailing observed performances of manufacturing processes in bioreactor devices. In some implementations, model component 110 may be configured to train the model until the model achieves a desired level of accuracy on the training information. In some implementations, the machine learning model may utilize one or more of an artificial neural network, naïve Bayes classifier algorithm, k-means clustering algorithm, support vector machine algorithm, linear regression, logistic regression, decision trees, random forest, nearest neighbors, and/or other approaches. Model component 110 may utilize training techniques such as deep learning. Model component may utilize training techniques such as one or more of supervised learning, reinforcement learning, and/or other techniques.

Input component 108 may obtain an input genomic construct and/or other information. The input genomic construct may specify a payload, a vector, and/or other elements. The payload may be a nucleic acid sequence defined by an order of nucleotides. The nucleic acid sequence may be characterized by one or more regions. The one or more regions may be distinguished based on the function provided by the order of nucleotides within the region. The regions may include a promoter region, one or more regulatory regions, a coding sequence (CDS), and/or other regions. The vector may indicate a backbone plasmid for storing and/or facilitating reproduction of the payload. The backbone plasmid may be a nucleic acid sequence defined by an order of nucleotides. The nucleic acid sequence(s) included in the input genomic construct may impact the formation of biological structures generated by the manufacturing process.

In some implementations, the input genomic construct may include a FASTA file, FASTQ file, BAM file, SAM file, BAS file, and/or other file types for storing the one or more nucleic acid sequences and/or other genomic information. The nucleic acid sequence(s) included in the input genomic construct may be an mRNA sequence, tRNA sequence, RNA sequence, DNA sequence, and/or other types of nucleic acid sequences. In some implementations, input component 108 may be configured to convert the input genomic construct from a first file type to a second file type to facilitate use by the stored model.

Input component 108 may obtain values of operational parameters associated with the bioreactor device and/or other information. The values of operational parameters may describe the bioreactor device, conditions of the biologically active environment house within the bioreactor device, and/or other aspects of the bioreactor device. By way of non-limiting illustration, descriptions of the conditions of the biologically active environment may include descriptions of contents included in the biologically active environment. In some implementations, the value of operation parameters associated with the bioreactor may be obtained from one or more users (e.g., via client computing platform(s) 104). In some implementations, the users may be provided with a set of default values of operational parameters. The default values of operational parameters may be modified by the users. In some implementations, input component 108 may be configured to determine recommended values of operational parameters based on the input genomic construct. The determination of recommended values may be based on empirical information describing observed manufacturing processes, previous uses of the stored model to generate predicted results of the manufacturing process, and/or other information.

The operational parameters may include settings, functions, contents, and/or other aspects related to the bioreactor device. The operational parameters may impact, influence, and/or otherwise affect the biochemical transformations and/or manufacturing processes performed within the bioreactor device. The values of operational parameters may be mathematical representations of the operational parameters. By way of non-limiting illustration, the aggregation of values of operational parameters may provide a mathematical model and/or representation of the bioreactor device.

The operational parameters may include one or more of a bioreactor device volume, temperature, acidity, pressure, and/or other aspects related to the bioreactor device. By way of non-limiting illustration, values of bioreactor device volume may include 10 L, 100 L, 100 L, and/or other volumes. In some implementations, the operational parameters may describe contents within the bioreactor and/or contents added to the bioreactor for use during the manufacturing process. Operational parameters describing contents within the bioreactor and/or contents added to the bioreactor may include a plasmid sequence, plasmid structure, plasmid molarity, plasmid concentration, transfection media, and/or other substances and/or other biochemical components.

Model component 110 may provide the input genomic construct, the values of operational parameters, and/or other information as input to the stored model(s). The model(s) may be configured to simulate the manufacturing process to determine predicted results of the manufacturing process. The simulation may be of the manufacturing process as performed in the biologically active environment housed within the bioreactor device as described by the values of operational parameters. In some implementations, the model(s) may calculate the impact of the individual values of operational parameters on the steps, operations, and/or transformations of the manufacturing process. The model(s) may determine the interactions between one or more values of operational parameters and/or the effect(s) of the interactions on the predicted results of the manufacturing process.

In some implementations, the model(s) may compare the inputs to the model with empirical information describing observed manufacturing processes to generate the predicted results of the simulated manufacturing process performed based on the inputs to the model(s). The observed manufacturing processes described by the empirical information may be the same as or similar to the simulated manufacturing process. By way of non-limiting illustration, the observed manufacturing processes may be performed in bioreactor devices that are the same as or similar to the bioreactor device described by the input values of operational parameters. The observed manufacturing processes may utilize genomic constructs that are the same as or similar to the input genomic construct.

In some implementations, the model(s) may identify one or more portions of the input genomic construct that may impact the predicted results of the manufacturing process. The portions may be subsequences of nucleotides within one or more nucleic acid sequences included in the input genomic construct. By way of non-limiting illustration, an individual identified portion of the input genomic construct may be a subsequence of nucleotides within the nucleic acid sequence encoding the vector, the payload, and/or other components of the input genomic construct. In some implementations, the one or more portions of the input genomic construct may be identified based on truncation propensity associated with the individual portion. Truncation propensity may indicate a likelihood of truncation occurring at and/or due to the individual portion and/or individual subsequence. Truncation occurrence(s) may result in defective, non-functioning, and/or otherwise deficient biological structures generated by the manufacturing process. In some implementations, the model may be configured to compare subsequences included in the input genomic construct with a list of subsequences. The list of subsequences may include one or more subsequences of nucleotides known to be associated with a high likelihood of truncation. The list of subsequences may be stored and/or obtained via electronic storage 128, obtained via external resources 126, and/or other components of system 100. Individual subsequences included in the input genomic construct may be identified responsive to being the same as or similar to one or more subsequences of the list of subsequences. In some implementations, the identification may be responsive to the similarity between the subsequences included in the input genomic construct and the subsequences of the list of subsequences meeting or exceeding a threshold.

Model component 110 may obtain outputs from the model(s). The outputs from the model(s) may include the predicted results of the manufacturing process based on a first simulation of the manufacturing process. The first simulation of the manufacturing process may be performed by the stored model(s). The first simulation of the manufacturing process may be associated with the inputs to the model(s). By way of non-limiting illustration, the first simulation of the manufacturing process may include computational and/or mathematical modeling of the manufacturing process utilizing the input genomic construct within the bioreactor described by the input values of operational parameters. The predicted results may describe expected biological structures to be generated by the manufacturing process. The predicted results may include information describing the simulated manufacturing process and/or other information. By way of non-limiting illustration, the predicted results may specify an efficiency score for the first simulation of the manufacturing process. The efficiency score may be based on a yield rate, uptake rate, and/or other information.

In some implementations, the expected biological structures generated by the manufacturing process may include viral vectors, non-viral vectors and/or other types of biological structures. The vectors may be formed for delivering genetic material to cells and/or perform other functions. The vectors may be characterized by a protein shell encapsulating genetic material and/or other contents. The genetic material may include the order of nucleotides defining the nucleic acid sequence of the input genomic construct (e.g., the payload) and/or other genetic material. The predicted results may describe aspects, functions, and/or other characteristics of the expected biological structures.

In some implementations, the predicted results of the manufacturing process may include a full-to-empty capsid ratio and/or other information. The full-to-empty capsid ratio may be determined by and/or calculated based on the predicted volume of vectors having protein shells encapsulating genetic material and the predicted volume of vectors having protein shells that do not encapsulate genetic material or encapsulate a portion of the genetic material. In some implementations, productivity (e.g., efficiency score) of the manufacturing process may be based on the full-to-empty capsid ratio. The predicted results may describe predicted truncations and/or other predicted activity occurring during the simulated manufacturing process.

In some implementations, the predicted results may describe the contents encapsulated within the protein shells of the generated vectors. By way of non-limiting illustration, the predicted results may characterize the vectors and/or genetic material encapsulated within the protein shells into one or more categories. The categories may include empty capsids, chimeric capsids, truncated genome capsids, complete genome capsids, and/or other characterizations. The predicted results may specify the predicted volume of biological structures belonging to the individual categories.

In some implementations, the outputs of the model(s) may include plasmid annotations corresponding to the input genomic construct. The plasmid annotations may indicate functional elements present in the nucleic acid sequences included in the nucleic genomic sequences of the input genomic construct. By way of non-limiting illustrations, the functional elements indicated by the plasmid annotations may include promoters, terminators, origins of replications, genes, and/or other types of functional elements. Individual plasmid annotations may specify a type of functional element, a location of the functional element (e.g., an index along the order of nucleotides), and/or other information. In some implementations, the plasmid annotations may be stored and/or outputted in a separate file.

Recommendation component 112 may generate recommendations based on the outputs of the model(s) and/or other information. The recommendations may be generated to increase productivity of the manufacturing process. The recommendations may specify modifications to at least one of the input genomic construct, the values of operational parameters, and/or other information provided as inputs to the model(s). By way of non-limiting illustration, modifications to the input genomic construct may include modifications to one or more nucleic acid sequences included in the input genomic construct. Modifications may include adding, removing, replacing, and/or otherwise changing the orders of nucleotides defining the one or more nucleic acid sequences. The modifications may be recommended to reduce truncation probability, increase the full-to-empty capsid ratio, and/or otherwise enhance productivity/efficiency of the manufacturing process. Increasing the full-to-empty capsid ratio may include increasing the volume of vectors having protein shells encapsulating genetic material. By way of non-limiting illustration, modifications to the values of operational parameters may include changing the values of the operational parameters to increase productivity/efficiency of the manufacturing process. In some implementations, the recommendations may be generated based on empirical information describing observed manufacturing processes, inputs/outputs from one or more other simulations of manufacturing processes generated by the stored model, and/or other information.

In some implementations, recommendation component 112 may be configured to modify the inputs to the model(s) based on the generated recommendations and/or other information. Modifying the inputs may include implementing the generated recommendations associated with at least one of the input genomic construct, the values of operational parameters, and/or other inputs to the model to generate modified inputs. Recommendation component 112 may be configured to provide the modified inputs to the stored model(s) and obtain output generated by the model(s) based on the modified inputs. The outputs from the model(s) may include the predicted results of the manufacturing process based on a second simulation of the manufacturing process. The second simulation of the manufacturing process may be performed based on the modified inputs to the model(s). The second simulation may include simulating the manufacturing process using the modified input genomic sequence within the bioreactor device described by the modified values of operational parameters.

The predicted results (based on the second simulation) may describe the expected biological structures to be generated by the manufacturing process. The expected biological structures to be generated by the manufacturing process according to the first simulation may be functionally analogous to the expected biological structures to be generated by the manufacturing process according to the second simulation. The term 'functionally analogous' may indicate the biological structures have the same or similar physical, chemical, biochemical, and/or pharmacological properties. In some implementations, the model may output a confidence score associated with the generated recommendations and/or other information. The confidence score may indicate a likelihood the predicted results of the manufacturing process may be achieved by implementation the generated recommendations.

In some implementations, recommendation component 112 may be configured to generate a comparison document. The comparison document may describe differences between the first simulation, the second simulation, and/or other simulations of the manufacturing process. The differences may include variance between the expected biological structures to be generated by the manufacturing process according to the first simulation, the expected biological structures to be generated by the manufacturing process according to the second simulation, and/or other expected biological structures. The document may include the full-to-empty capsid ratio and/or other information associated with the outputs.

Output component 114 may be configured to provide the outputs from the model(s), the generated recommendations, and/or other information. In some implementations, output component 114 may be configured to store the outputs from the model(s), generated recommendations, and/or other information in electronic storage 128. In some implementations, output component 114 may be configured to provide the outputs from the model(s), the generated recommendations, and/or other information via a user interface (e.g., via client computing platform(s) 104). In some implementations, output component 114 may be configured to aggregate individual outputs from the one or more stored models and/or provide the aggregated outputs. The user interface may be configured to present graphical display(s) of the outputs from the model(s) and/or other information. By way of non-limiting illustration, the user interface may be configured to display information included in the generated comparison document. In some implementations, user interface elements may be selectable to present the differences between the first simulation and the second simulation or hide the differences. User interface elements may be selectable to present expanded views and/or to present hidden information (e.g., information included in the output obtained from the model).

Figure 3:
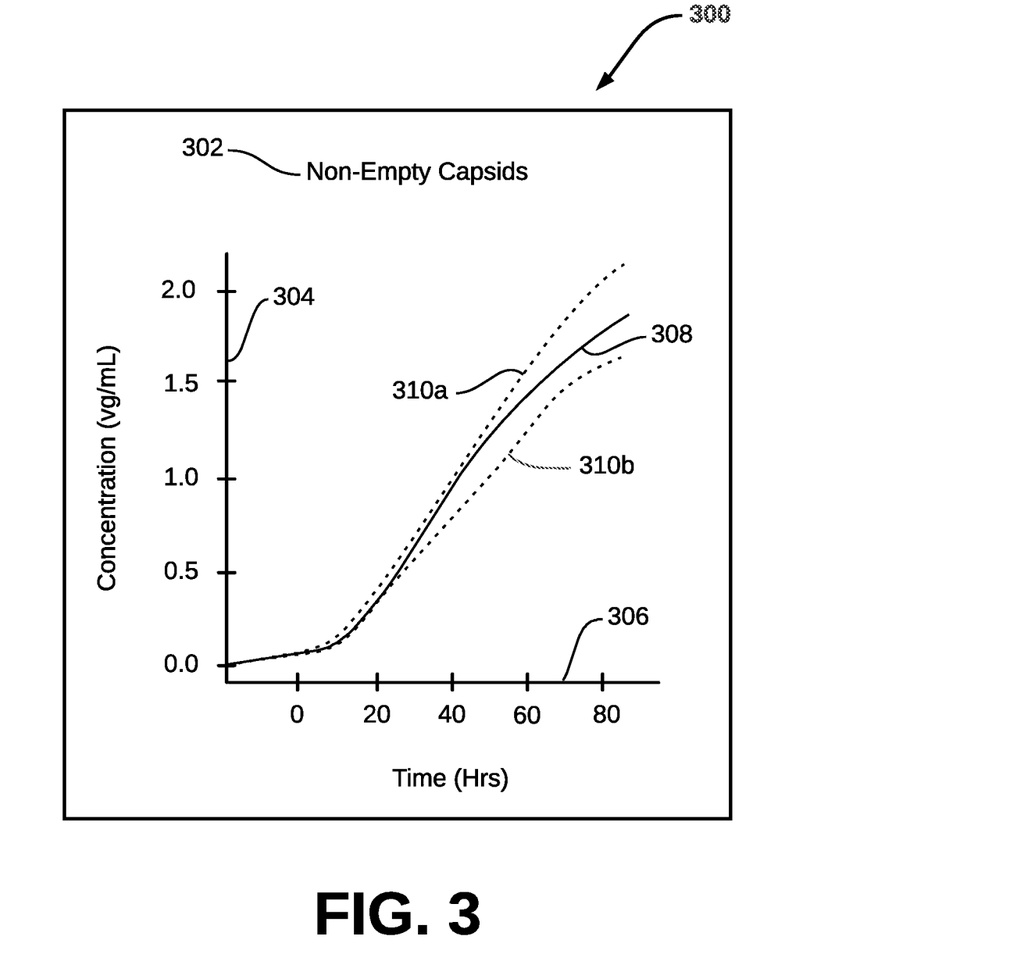
FIG. 3 illustrates an exemplary user interface, in accordance with one or more implementations.

FIG. 3 illustrates a user interface 300, in accordance with one or more implementations. User interface 300 may be configured to effectuate presentations of output obtained from a model. User interface 300 may include one or more user interface elements for displaying the obtained output. By way of non-limiting illustration, user interface 300 may include a graph 302 for displaying the predicted results of the manufacturing process. In some implementations, graph 302 may include one or more selectable elements for effectuating expanded views and/or other information included in the obtained output. Graph 302 may include a first axis 304, a second axis 306, and/or other components. First axis 304 may correspond to a concentration of biological structures to be generated by the manufacturing process. By way of non-limiting illustration, the biological structures to be generated by the manufacturing process may include non-empty capsids. Second axis 306 may correspond to duration of the manufacturing process (e.g., hours). Graph 302 may display the concentration of non-empty capsids to be generated at one or more times during the manufacturing process. Graph 302 may include one or more lines for displaying the concentration of non-empty capsids to be generated during the manufacturing process. Graph 302 may include a first line 308, a second line 310*a*, a third line 310*b*, and/or other elements. First line 308 may correspond to the predicted results of the manufacturing process (i.e., the concentration of non-empty capsids throughout the manufacturing process). Second and third lines 310*a-b* may correspond to the range of predicted results of the manufacturing process.

Figure 4:
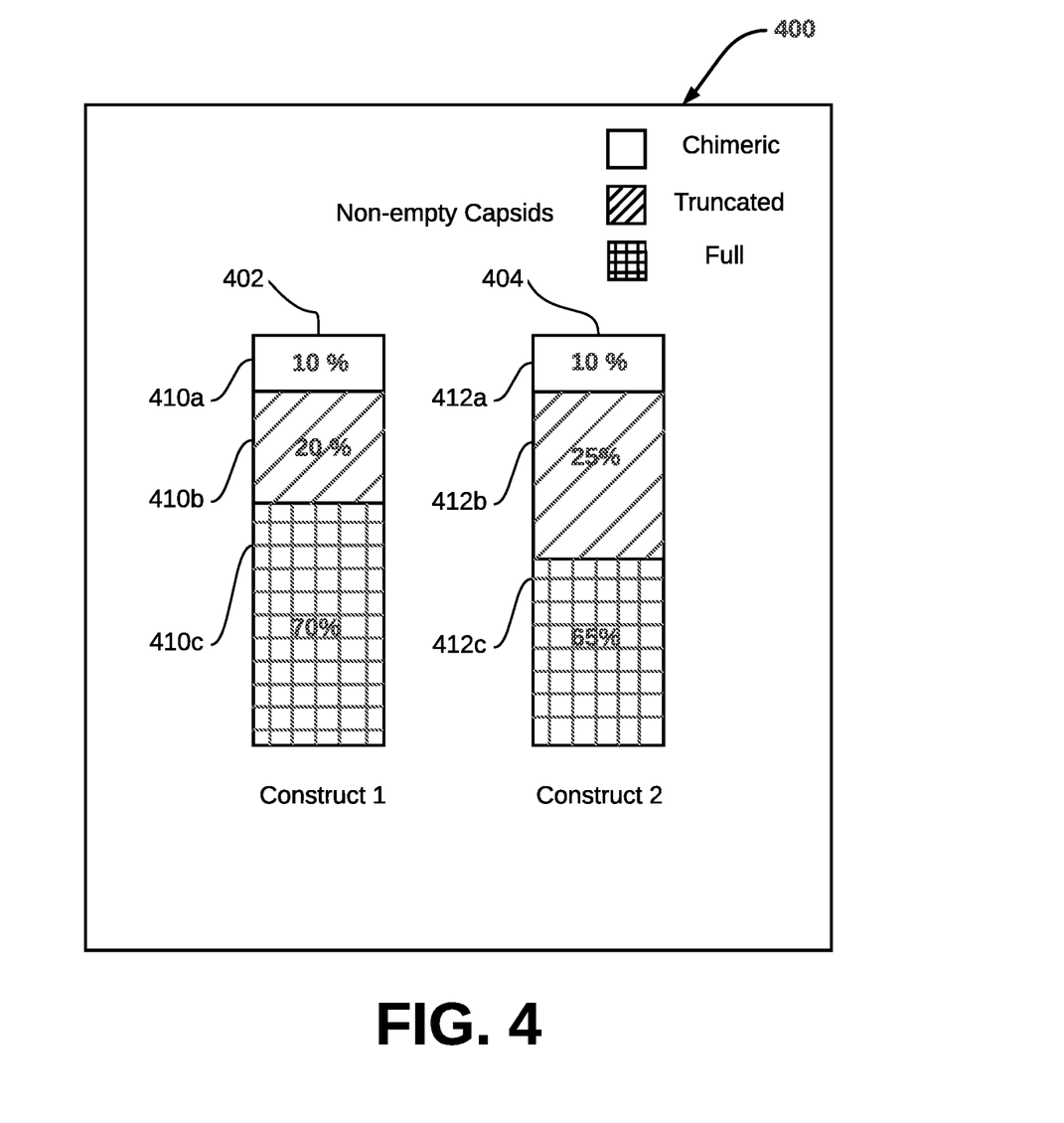
FIG. 4 illustrates an exemplary user interface, in accordance with one or more implementations.

FIG. 4 illustrates a user interface 400, in accordance with one or more implementations. User interface 400 may be configured to effectuate presentations of outputs obtained from a model. User interface 400 may include one or more user interface elements for displaying the obtained outputs. User interface 400 may include a first interface element 402, a second interface element 404, and/or other user interface elements. First interface element 402 may display outputs obtained from the model based on a first simulation of the manufacturing process. The first simulation may be based on first input to the model. The first input to the model may include a first genomic construct ('Construct 1'), a first set of values of operational parameters, and/or other inputs. The second simulation may be based on a second simulation of the manufacturing process. The second simulation may be based on second input to the model. The second input to the model may include a second genomic construct ('Construct 2'), a second set of values of operational parameters, and/or other inputs. In some implementations, the second input to the model may be obtained via modification to the first input (e.g., using generated recommendations specifying modifications).

The predicted results may include the predicted volumes for one or more categories of non-empty capsids (e.g., chimeric, truncated, full, etc.). First interface element 402 may include one or more elements 410*a-c* for displaying the predicted results of the first simulation of the manufacturing process. By way of non-limiting illustration, first element 410*a* may correspond to the predicted volume of chimeric capsids included in the predicted results of the first simulation. Second element 410*b* may correspond to the predicted volume of truncated capsids included in the predicted results of the first simulation. Third element 410*c* may correspond to the predicted volume of full capsids included in the predicted results of the first simulation.

Second interface elements 404 may include one or more elements 412*a-c* for displaying the predicted results of the second simulation of the manufacturing process. By way of non-limiting illustration, fourth element 412*a* may correspond to the predicted volume of chimeric capsids included in the predicted results of the second simulation. Fifth element 412*b* may correspond to the predicted volume of truncated capsids included in the predicted results of the second simulation. Sixth element 412*c* may correspond to the predicted volume of full capsids included in the predicted results of the second simulation.

In some implementations, server(s) 102, client computing platform(s) 104, and/or external resources 126 may be operatively linked via one or more electronic communication links. For example, such electronic communication links may be established, at least in part, via a network 116 such as the Internet and/or other networks. It will be appreciated that this is not intended to be limiting, and that the scope of this disclosure includes implementations in which server(s) 102, client computing platform(s) 104, and/or external resources 126 may be operatively linked via some other communication media.

A given client computing platform 104 may include one or more processors configured to execute computer program components. The computer program components may be configured to enable an expert or user associated with the given client computing platform 104 to interface with system 100 and/or external resources 126 and/or provide other functionality attributed herein to client computing platform(s) 104. By way of non-limiting example, the given client computing platform 104 may include one or more of a desktop computer, a laptop computer, a handheld computer, a tablet computing platform, a Smartphone, and/or other computing platforms.

External resources 126 may include sources of information outside of system 100, external entities participating with system 100, and/or other resources. In some implementations, some or all of the functionality attributed herein to external resources 126 may be provided by resources included in system 100.

Server(s) 102 may include communication lines, or ports to enable the exchange of information with a network 116 and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 128 may comprise non-transitory storage media that electronically stores information. The electronic storage media of electronic storage 128 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 128 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 128 may include one or more virtual storage resources (e.g., cloud storage, a virtual private network, and/or other virtual storage resources). Electronic storage 128 may store software algorithms, information determined by processor(s) 130, information received from server(s) 102, information received from client computing platform(s) 104, and/or other information that enables server(s) 102 to function as described herein.

Processor(s) 130 may be configured to provide information processing capabilities in server(s) 102. As such, processor(s) 130 may include one or more of a digital processor, an analog processor, a digital circuit designed to process information, an analog circuit designed to process information, a state machine, and/or other mechanisms for electronically processing information. Although processor(s) 130 is shown in FIG. 1 as a single entity, this is for illustrative purposes only. In some implementations, processor(s) 130 may include a plurality of processing units. These processing units may be physically located within the same device, or processor(s) 130 may represent processing functionality of a plurality of devices operating in coordination. Processor(s) 130 may be configured to execute components 108, 110, 112, 114, and/or other components. Processor(s) 130 may be configured to execute components 108, 110, 112, 114, and/or other components by software; hardware; firmware; some combination of software, hardware, and/or firmware; and/or other mechanisms for configuring processing capabilities on processor(s) 130. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, and/or 114 are illustrated in FIG. 1 as being implemented within a single processing unit, in implementations in which processor(s) 130 includes multiple processing units, one or more of components 108, 110, 112, and/or 114 may be implemented remotely from the other components. The description of the functionality provided by the different components 108, 110, 112, and/or 114 described below is for illustrative purposes, and is not intended to be limiting, as any of components 108, 110, 112, and/or 114 may provide more or less functionality than is described. For example, one or more of components 108, 110, 112, and/or 114 may be eliminated, and some or all of its functionality may be provided by other ones of components 108, 110, 112, and/or 114. As another example, processor(s) 130 may be configured to execute one or more additional components that may perform some or all of the functionality attributed below to one of components 108, 110, 112, and/or 114.

Figure 2:
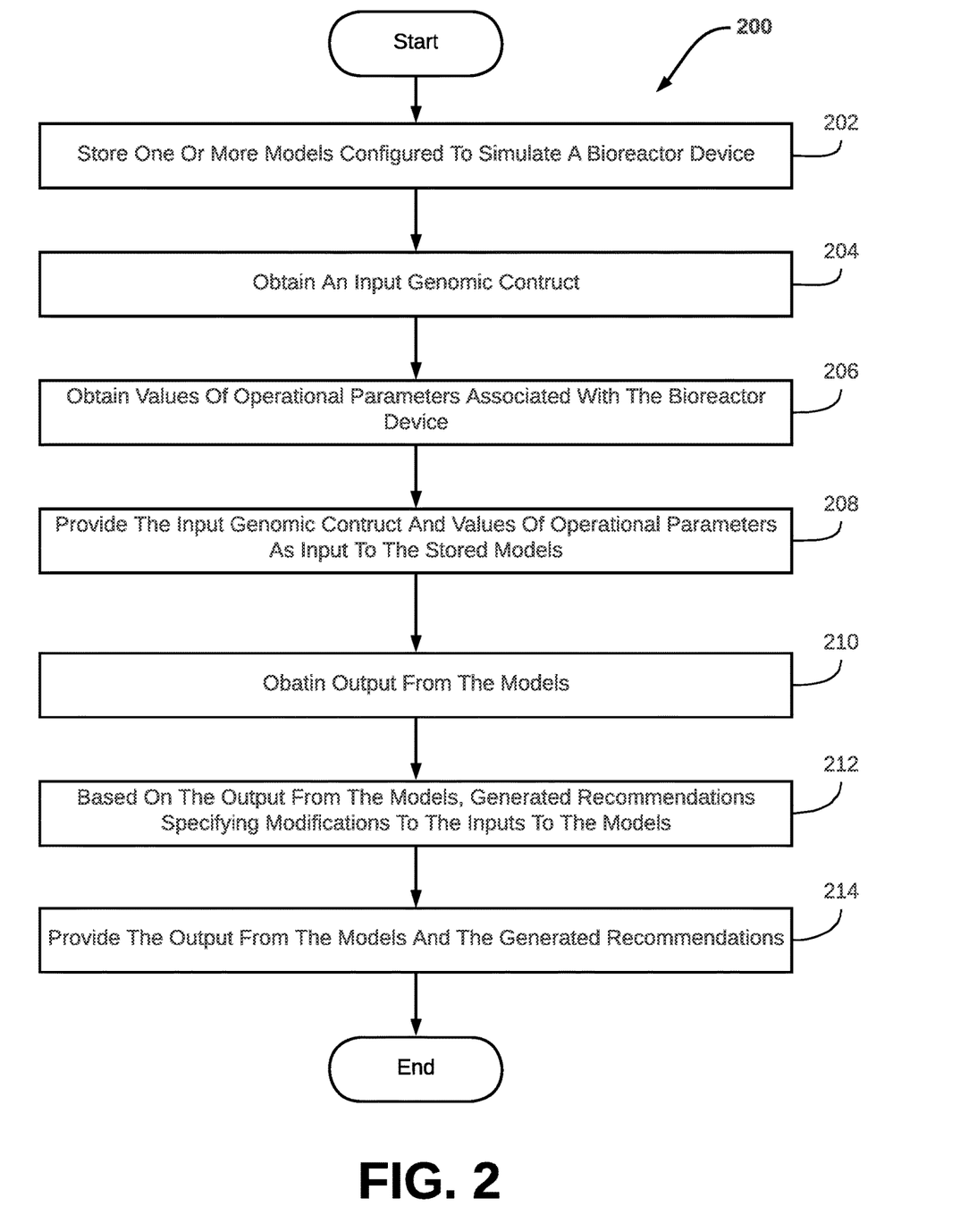
FIG. 2 illustrates a method for predicting results of a manufacturing process for generating biological structures, in accordance with one or more implementations.

FIG. 2 illustrates a method 200 for predicting results of a manufacturing process for generating biological structures, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include storing one or more models configured to simulate a bioreactor device to determine predicted results of a manufacturing process to generate biological structures. The bioreactor device may house a biologically active environment that supports biochemical transformations. The manufacturing process may be performed in the biologically active environment housed within the bioreactor device. Inputs to the model may include a genomic construct, values of operational parameters associated with the bioreactor device, and/or other information. Outputs of the model(s) may specify the predicted results of the manufacturing process and/or other information. Operation 202 may be performed by one or more hardware processors configured by machine-readable instructions including a component that is the same as or similar to electronic storage 128, in accordance with one or more implementations.

An operation 204 may include obtaining an input genomic construct and/or other information. The input genomic construct may include a nucleic acid sequence defined by an order of nucleotides. The nucleic acid sequence may impact the formation of biological structures generated by the manufacturing process. Operation 204 may be performed by one or more hardware processors configured by machine-readable instructions including a component that is the same as or similar to input component 108, in accordance with one or more implementations.

An operation 206 may include obtaining values of operational parameters associated with the bioreactor device and/or other information. The values of operational parameters may describe the bioreactor device, conditions of the biologically active environment house within the bioreactor device, and/or other aspects of the bioreactor device. Descriptions of the conditions of the biologically active environment may include descriptions of contents included in the biologically active environment. Operation 206 may be performed by one or more hardware processors configured by machine-readable instructions including a component that is the same as or similar to input component 108, in accordance with one or more implementations.

An operation 208 may include providing the input genomic construct, the values of operational parameters, and/or other information as input to the stored model(s). The model may be configured to simulate the manufacturing process. The simulation may be of the manufacturing process as performed in the biologically active environment housed within the bioreactor device as described by the values of operational parameters. The model(s) may simulate the manufacturing process to determine the predicted results of the manufacturing process. Operation 208 may be performed by one or more hardware processors configured by machine-readable instructions including a component that is the same as or similar to model component 110, in accordance with one or more implementations.

An operation 210 may include obtaining outputs from the model(s). The outputs from the model(s) may include the predicted results of the manufacturing process based on a first simulation of the manufacturing process. The results may describe expected biological structures to be generated by the manufacturing process. Operation 210 may be performed by one or more hardware processors configured by machine-readable instructions including a component that is the same as or similar to model component 110, in accordance with one or more implementations.

An operation 212 may include generating recommendations based on the outputs of the model(s) and/or other information. The recommendations may specify modifications to at least one of the input genomic construct, the values of operational parameters, and/or other information provided as inputs to the model(s). The recommendations may be generated to increase productivity of the manufacturing process. Operation 212 may be performed by one or more hardware processors configured by machine-readable instructions including a component that is the same as or similar to recommendation component 112, in accordance with one or more implementations.

An operation 214 may include providing the outputs from the model(s), the generated recommendations, and/or other information. Operation 214 may be performed by one or more hardware processors configured by machine-readable instructions including a component that is the same as or similar to output component 114, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed:

1. A system configured to generate recommendations based on predicted results of a manufacturing process for generating biological structures, the system comprising:
    electronic storage that stores one or more trained machine-learning models configured to determine predicted results of a manufacturing process that generates biological structures within a bioreactor device, wherein the bioreactor device houses a biologically active environment that supports biochemical transformations, wherein the manufacturing process is performed in the biologically active environment housed within the bioreactor device, wherein inputs to the trained machine-learning models include a genomic construct and values of operational parameters associated with the bioreactor device, and wherein outputs of the one or more trained machine-learning models specify the predicted results of the manufacturing process;
    one or more physical processors configured by machine-readable instructions to:
        obtain, via user input, a first input genomic construct, wherein the first input genomic construct includes a nucleic acid sequence defined by an order of nucleotides, wherein the nucleic acid sequence impacts the formation of biological structures generated by the manufacturing process;
        obtain, via user input, a first set of values of operational parameters associated with the bioreactor device, wherein the first set of values of operational parameters describes the bioreactor device and conditions of the biologically active environment house within the bioreactor device, and wherein descriptions of the conditions of the biologically active environment include descriptions of contents within the biologically active environment;
        provide the first input genomic construct and the first set of values of operational parameters as input to the one or more trained machine-learning models, wherein the one or more trained machine-learning models are configured to generate predicted results of the manufacturing process performed in the biologically active environment housed within the bioreactor device as described by the first set of values of operational parameters;
        obtain a first output from the one or more trained machine-learning models, wherein the first output from the one or more trained machine-learning models include the predicted results of the manufacturing process based on the first input genomic construct and the first set of values of operational parameters, and wherein the results describe expected biological structures to be generated by the manufacturing process;
        generate recommendations based on the first output of the one or more trained machine-learning models, wherein the recommendations specify modifications to at least one of the first input genomic construct and the first set of values of operational parameters provided as inputs to the one or more trained machine-learning models, wherein the recommendations are generated to increase productivity of the manufacturing process;
        modify the first genomic construct and the first set of values of operations parameters based on the recommendations to generate a modified genomic construct and a modified set of values of operational parameters;
        provide the modified genomic construct and the modified set of values of operational parameters to the one or more trained machine-learning models;
        obtain a second output from the one or more trained machine-learning models, wherein the second output from the one or more trained machine-learning models includes the predicted results of the manufacturing process based on the modified genomic construct and the modified set of values of operational parameters; and present, via a user interface, the first output and the second output to a user, wherein the presentation displays differences between the first output and the second output.

2. The system of claim 1, wherein the expected biological structures generated by the manufacturing process include viral vectors for delivering genetic material, wherein the viral vectors are characterized by a protein shell encapsulating genetic material, and wherein the genetic material includes the order of nucleotides defining the nucleic acid sequence of the input genomic construct.

3. The system of claim 2, wherein the predicted results of the manufacturing process includes a full-to-empty capsid ratio, wherein the full-to-empty capsid ratio is determined by a predicted volume of viral vectors having protein shells encapsulating genetic material and a predicted volume of viral vectors having protein shells that do not encapsulate genetic material or encapsulate a portion of the genetic material.

4. The system of claim 3, wherein productivity of the manufacturing process is based on the full-to-empty capsid ratio, and wherein the recommendations are generated to increase the volume of viral vectors having protein shells encapsulating genetic material.

5. The system of claim 1, wherein the one or more physical processors are further configured by machine-readable instructions to:

generate a comparison document, wherein the comparison document describes differences between the first output and the second output, wherein the differences include variance between the expected biological structures to be generated by the manufacturing process performed in the biologically active environment housed within the bioreactor device as described by the first set of values of operational parameters and the expected biological structures to be generated by the manufacturing process performed in the biologically active environment housed within the bioreactor device as described by the modified set of values of operational parameters.

6. The system of claim 1, wherein the expected biological structures to be generated by the manufacturing process performed in the biologically active environment housed within the bioreactor device as described by the first set of values of operational parameters are functionally analogous to the expected biological structures to be generated by the manufacturing process performed in the biologically active environment housed within the bioreactor device as described by the modified set of values of operational parameters.

7. The system of claim 1, wherein the operational parameters include one or more of bioreactor device volume, temperature, acidity, pressure, cell count, plasmid sequences, and plasmid concentration.

8. A method for generating recommendations based on predicted results of a manufacturing process for generating biological structures, the method comprising:

storing one or more trained machine-learning configured to determine predicted results of a manufacturing process that generates biological structures within a bioreactor device, wherein the bioreactor device houses a biologically active environment that supports biochemical transformations, wherein inputs to the models include a genomic construct and values of operational parameters associated with the bioreactor device, and wherein outputs of the one or more trained machine-learning models specify the predicted results of the manufacturing process;

obtaining, via user input, a first input genomic construct, wherein the first input genomic construct includes a nucleic acid sequence defined by an order of nucleotides, wherein the nucleic acid sequence impacts the formation of biological structures generated by the manufacturing process;

obtaining, via user input, a first set of values of operational parameters associated with the bioreactor device, wherein the first set of values of operational parameters describes the bioreactor device and conditions of the biologically active environment housed within the bioreactor device, and wherein descriptions of the conditions of the biologically active environment include descriptions of contents within the biologically active environment;

providing the first input genomic construct and the first set of values of operational parameters as input to the stored model, wherein the one or more trained machine-learning models are configured to generate predicted results of the manufacturing process performed in the biologically active environment housed within the bioreactor device as described by the first set of values of operational parameters;

obtaining first output from the one or more trained machine-learning models, wherein the first output from the one or more trained machine-learning models include the predicted results of the manufacturing process based on the first input genomic construct and the first set of values of operational parameters, and wherein the results describe expected biological structures to be generated by the manufacturing process;

generating recommendations based on the first output of the one or more trained machine-learning models, wherein the recommendations specify modifications to at least one of the first input genomic construct and the first set of values of operational parameters provided as input to the one or more trained machine-learning models, wherein the recommendations are generated to increase productivity of the manufacturing process;

modifying the first genomic construct and the first set of values of operations parameters based on the recommendations to generate a modified genomic construct and a modified set of values of operational parameters;

providing the modified genomic construct and the modified set of values of operational parameters to the one or more trained machine-learning models;

obtaining a second output from the one or more trained machine-learning models, wherein the second output from the one or more trained machine-learning models includes the predicted results of the manufacturing process based on the modified genomic construct and the modified set of values of operational parameters; and presenting the first output and the second output to a user, wherein the presentation displays differences between the first output and the second output.

9. The method of claim 8, wherein the expected biological structures generated by the manufacturing process include viral vectors for delivering genetic material, wherein the viral vectors are characterized by a protein shell encapsulating genetic material, and wherein the genetic material includes the order of nucleotides defining the nucleic acid sequence of the input genomic construct.

10. The method of claim 9, wherein the predicted results of the manufacturing process includes a full-to-empty capsid ratio, wherein the full-to-empty capsid ratio is determined by a predicted volume of viral vectors having protein shells encapsulating genetic material and a predicted volume of viral vectors having protein shells that do not encapsulate genetic material or encapsulate a portion of the genetic material.

11. The method of claim 10, wherein productivity of the manufacturing process is based on the full-to-empty capsid ratio, and wherein the recommendations are generated to increase the volume of viral vectors having protein shells encapsulating genetic material.

12. The method of claim 8, wherein the method further comprises:
generating a comparison document, wherein the comparison document describes differences between the first output and the second output, wherein the differences include variance between the expected biological structures to be generated by the manufacturing process performed in the biologically active environment housed within the bioreactor device as described by the first set of values of operational parameters and the expected biological structures to be generated by the manufacturing process performed in the biologically active environment housed within the bioreactor device as described by the modified set of values of operational parameters.

13. The method of claim 8, wherein the expected biological structures to be generated by the manufacturing process performed in the biologically active environment housed within the bioreactor device as described by the first set of values of operational parameters are functionally analogous to the expected biological structures to be generated by the manufacturing process performed in the biologically active environment housed within the bioreactor device as described by the modified set of values of operational parameters.

14. The method of claim 8, wherein the operational parameters include one or more of bioreactor device volume, temperature, acidity, pressure, cell count, plasmid sequences, and plasmid concentration.

* * * * *

UNITED STATES PATENT AND TRADEMARK OFFICE
CERTIFICATE OF CORRECTION

| | | |
|---|---|---|
| PATENT NO. | : 12,106,827 B1 | Page 1 of 1 |
| APPLICATION NO. | : 18/335875 | |
| DATED | : October 1, 2024 | |
| INVENTOR(S) | : Andrew Busey et al. | |

It is certified that error appears in the above-identified patent and that said Letters Patent is hereby corrected as shown below:

In the Claims

In Claim 1, Column 14, Line 41, please replace "include" with --includes--, therefor.

In Claim 8, Column 16, Line 31, please replace "include" with --includes--, therefor.

Signed and Sealed this
Seventeenth Day of December, 2024

Derrick Brent
*Acting Director of the United States Patent and Trademark Office*